United States Patent

Cotteret et al.

[11] Patent Number: 5,518,506
[45] Date of Patent: May 21, 1996

[54] PROCESS FOR DYEING KERATINOUS FIBRES WITH AN ALKALINE COMPOSITION CONTAINING PARA-AMINOPHENOLS SUBSTITUTED IN POSITION 2 IN COMBINATION WITH 6- OR 7-HYDROXINDOLE

[75] Inventors: Jean Cotteret, Verneuil-sur-Seine; Marie P. Audousset, Levallois-Perret, both of France

[73] Assignee: L'Oreal, Paris, France

[21] Appl. No.: 458,236

[22] Filed: Jun. 2, 1995

Related U.S. Application Data

[63] Continuation of Ser. No. 162,080, Dec. 9, 1993 which is a PCT/FR93/00349, apr. 7, 1993.

[30] Foreign Application Priority Data

Apr. 9, 1992 [FR] France ............... 92 04346

[51] Int. Cl.$^6$ .................................................. A61K 7/13
[52] U.S. Cl. .................. 8/409; 8/406; 8/407; 8/408; 8/411; 8/412; 8/421; 8/423
[58] Field of Search ...................... 8/405, 406, 407, 8/408, 409, 412, 421, 423, 411

[56] References Cited

U.S. PATENT DOCUMENTS

| | | | |
|---|---|---|---|
| 4,997,451 | 3/1991 | Calusen et al. | 8/412 |
| 5,034,015 | 7/1991 | Junino et al. | 8/423 |
| 5,053,052 | 10/1991 | Junino et al. | 8/412 |
| 5,202,487 | 4/1993 | Junino et al. | 8/412 |
| 5,207,798 | 5/1993 | Cotteret et al. | 8/423 |
| 5,279,620 | 1/1994 | Junino et al. | 8/409 |

*Primary Examiner*—Paul Lieberman
*Assistant Examiner*—Caroline L. Dusheck
*Attorney, Agent, or Firm*—Jacobson, Price, Holman & Stern

[57] ABSTRACT

A process for dyeing keratinous fibres, wherein a mixture of at least one para-aminophenol of formula:

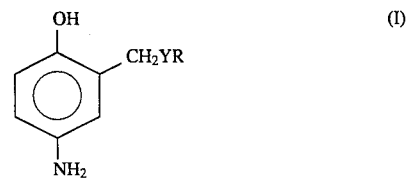

in which,

Y is oxygen or sulphur,

R is alkyl, monohydroxyalkyl, polyhydroxyalkyl, or their acid addition salts, and 6-hydroxyindole, 7- hydroxyindole or mixtures thereof, is applied to the fibers, the colour being developed at alkaline pH with an oxidising agent.

21 Claims, No Drawings

PROCESS FOR DYEING KERATINOUS FIBRES WITH AN ALKALINE COMPOSITION CONTAINING PARA-AMINOPHENOLS SUBSTITUTED IN POSITION 2 IN COMBINATION WITH 6- OR 7-HYDROXINDOLE

This is a continuation of application Ser. No. 08/162,080, filed Dec. 9, 1993 which is a PCT/FR93/00349, Apr. 7, 1993.

The present invention relates to a new process for dyeing keratinous fibres and in particular human keratinous fibres, using para-aminophenol substituted in position 2 in combination with 6- or 7-hydroxyindole and an oxidising agent in alkaline medium, and to the compositions used during this process.

It is known to dye keratinous fibres and in particular human hair with dyeing compositions containing oxidation dye precursors, in particular ortho- or para-phenylenediamines, ortho- or para-aminophenols, generally called "oxidation bases", and couplers, also called colouring modifiers, more particularly aromatic meta-phenylenediamines, meta-aminophenols and metadiphenols, which make it possible to modify and enrich with highlights the "base" colourings obtained with the condensation products of the oxidation bases.

Research, in the field of oxidation hair dyeing, is for oxidation dye precursors and couplers which make it possible to confer on hair a colouring having a satisfactory resistance to light, washings, bad weather, perspiration and to the various treatments which hair may be subjected to, and to obtain a wide range of colouring shades.

The para-aminophenols substituted in position 2, and their use in dyeing compositions for keratinous fibres in combination with standard couplers of benzene type are known and described in the patent FR 2,637,282.

A dyeing process for dyeing keratinous fibres in acid medium is described in the patent FR 2,659,228 of the Applicant as using a composition containing, as coupler, 6-hydroxyindole, 7-hydroxyindole or their derivatives with oxidation dye precursors such as paraaminophenols. However, such a process did not provide, after application to the fibres, a sufficiently resistant colouring.

In the patent FR 2,636,236, the Applicant describes dyeing compositions for dyeing keratinous fibres in alkaline medium, containing 6-hydroxyindole or 7-hydroxyindole as coupler combined with an oxidation base including para-aminophenol and some of its derivatives. The colourings obtained with these compositions did not exhibit a satisfactory resistance, especially to light.

The Applicant has discovered, which forms the subject of the invention, that the use of certain para-aminophenols substituted in position 2 as oxidation dye precursors in combination with 6-hydroxyindole or 7-hydroxyindole and of an oxidising agent makes it possible to obtain, in alkaline medium, after application to keratinous fibres and in particular human hair, a wide range of colourings with warm shades exhibiting a resistance to light, to washings and to bad weather, to perspiration and to the various treatments which hair may be subjected to, which is particularly outstanding and greater than those of the prior art.

The subject of the present invention is thus a process for dyeing keratinous fibres, in particular human keratinous fibres such as hair, comprising the application to these fibres of at least, as oxidation dye precursor, one para-aminophenol substituted in position 2 of formula (I) below, as coupler, 6-hydroxyindole or 7-hydroxyindole and one oxidising agent, at alkaline pH.

Another subject of the invention is a dyeing agent containing two components, one of the components of which comprises the oxidation dye precursor of formula (I) defined below and 6- or 7-hydroxyindole, and the other the oxidising agent.

Another subject of the invention applies to the ready-to-use composition containing the various agents used for dyeing keratinous fibres in alkaline medium.

Another subject of the invention is dyeing requisites or "kits", containing several components, which make possible the use of the process indicated above.

Other subjects of the invention will become apparent on reading the description and examples which follow.

The process for dyeing keratinous fibres and in particular human keratinous fibres such as hair in accordance with the invention is essentially characterised-in that there is applied to these fibres at least one para-aminophenol substituted in position 2 of formula (I)

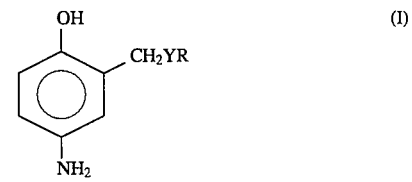

in which:
Y represents an oxygen atom or sulphur atom, R represents a $C_1$-$C_4$ alkyl, $C_1$-$C_4$ monohydroxyalkyl or $C_2$-$C_4$ polyhydroxyalkyl radical, and their addition salts with an acid; 6-hydroxyindole and/or 7-hydroxyindole; the colour being displayed at a pH greater than 7 using an oxidising agent.

According to the process in accordance with the invention, there is applied to keratinous fibres and in particular human keratinous fibres at least one composition (A) containing, in a medium suitable for dyeing, at least one para-aminophenol substituted in position 2 of formula (I) defined above as oxidation dye precursor, in combination with 6-hydroxyindole and/or 7-hydroxyindole as coupler, the colour being displayed at alkaline pH using an oxidising agent present in the composition (A) or applied separately simultaneously or sequentially by means of a composition (B) containing it in a medium suitable for dyeing.

Among the preferred meanings of the radical R in the para-aminophenol compounds of general formula (I), the $C_1$-$C_4$ alkyl radical denotes the methyl, ethyl, propyl, isopropyl, butyl or isobutyl radicals and the mono- or polyhydroxyalkyl radical denotes —$CH_2$—$CH_2OH$, —$CH_2$—$CHOH$—$CH_2$—$OH$ or —$CH_2$—$CHOH$—$CH_3$.

The acid salts corresponding to the para-aminophenol compounds of general formula (I) are preferably chosen from the hydrochlorides, the sulphates, the hydrobromides or the tartrates.

Among the para-aminophenols of general formula (I), there may be mentioned the following compounds:
2-methoxymethyl-4-aminophenol,
2-ethoxymethyl-4-aminophenol,
2-propoxymethyl-4-aminophenol,
2-isopropoxymethyl-4-aminophenol,
2-(β-hydroxyethoxymethyl)-4-aminophenol,
2-methylthiomethyl-4-aminophenol,
2-(β-hydroxyethylthiomethyl)-4-aminophenol,
2-(β, γ-dihydroxypropylthiomethyl)-4-aminophenol, and their salts.

Among the preferred compounds of formula (I), there may be mentioned:
2-methoxymethyl-4-aminophenol
2-ethoxymethyl-4-aminophenol 2-(β-hydroxyethoxymethyl)-4-aminophenol
2-methylthiomethyl-4-aminophenol and their salts.

According to the process of the invention, 6-hydroxyindole is preferably used, in combination with the para-aminophenol of general formula (I) defined above, as coupler.

The oxidising agent is preferably chosen from hydrogen peroxide, urea hydrogen peroxide, alkali metal bromates, or persalts such as the perborates and the persulphates. Hydrogen peroxide is particularly preferred.

The composition (A) which contains, as oxidation dye precursor, at least one para-aminophenol of formula (I) and 6-hydroxyindole and/or 7-hydroxyindole as coupler can have a pH of between 3 and 10.5 and can be adjusted to the chosen value by means of basifying agents generally used in dyeing keratinous fibres, such as aqueous ammonia, alkali metal carbonates, alkanolamines such as the mono-, di- and triethanolamines and their derivatives, or sodium or potassium hydroxide, or standard acidifying agents, such as inorganic or organic acids, such as hydrochloric, tartaric, citric and phosphoric acids.

The pH of the composition (B) containing the oxidising agent as defined above is such that, after mixing with the composition A, the pH of the mixture is greater than 7 and preferably of between 8 and 11.

The compounds of formula (I) are present in the composition applied to keratinous fibres in proportions preferably of between 0.05 and 3.5% by weight with respect to the total weight of the composition; 6-hydroxyindole and/or 7-hydroxyindole are present therein in proportions of between 0.01 and 4% by weight with respect to the total weight of the composition.

The dyeing compositions defined above and used in the dyeing process of the invention can also contain, in addition to the para-aminophenol of formula (I) defined above, other para and/or ortho oxidation dye precursors known in themselves.

These oxidation dye precursors of ortho or para type can be chosen from para-phenylenediamines, paraaminophenols other than those of formula (I), paraheterocyclic precursors derived from pyridine or from pyrimidine, such as 2,5-diaminopyridine, 2-hydroxy- 5-aminopyridine, 2,4,5,6-tetraaminopyrimidine, 4,5-diamino-l-methylpyrazole or 2-dimethylamino- 4,5,6-triaminopyrimidine, ortho-aminophenols and the so-called "double" bases.

As para-phenylenediamines, there may more particularly be mentioned the compounds corresponding to the formula (II):

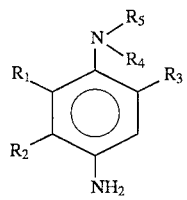

in which:

$R_1$, $R_2$ and $R_3$, which are identical or different, represent a hydrogen or halogen atom, a $C_1$-$C_4$ alkyl radical, a $C_1$-$C_4$ alkoxy radical, a $C_1$-$C_4$ hydroxyalkyl radical, a carboxyl radical or a sulpho radical;

$R_4$ and $R_5$, which are identical or different, represent a hydrogen atom, or an alkyl, hydroxyalkyl, alkoxyalkyl, carbamoylalkyl, mesylaminoalkyl, acetylaminoalkyl, ureidoalkyl, carbalkoxyaminoalkyl, sulphoalkyl, piperidinoalkyl, morpholinoalkyl or phenyl radical, the phenyl optionally being substituted in the para position by an amino group, or else $R_4$ and $R_5$ form, Jointly with the nitrogen atom to which they are bonded, a piperidino or morpholino heterocycle, with the proviso that $R_1$ or $R_3$ represents a hydrogen atom when $R_4$ and $R_5$ do not represent a hydrogen atom, and the salts of its compounds. These alkyl or alkoxy groups have from 1 to 4 carbon atoms and denote especially methyl, ethyl, propyl, methoxy and ethoxy.

Among compounds of formula (II), there may be mentioned para-phenylenediamine, p-toluylenediamine, methoxy-para-phenylenediamine, chloro-para-phenylenediamine, 2,3-dimethyl-para-phenylenediamine, 2,6-dimethyl-para-phenylenediamine, 2,6 -diethyl-para-phenylenediamine, 2,5-dimethyl-para-phenylenediamine, 2-methyl-5-methoxy-para-phenylenediamine, 2,6-dimethyl-5-methoxy-para-phenylendiamine, N,N-dimethyl-para-phenylenediamine, N,N-diethyl-para-phenylenediamine, N,N-dipropyl-para-phenylenediamine, 3-methyl-4-amino-N,N-diethylaniline, N,N-di(β-hydroxyethyl)-para-phenylenediamine, 3-methyl- 4-amino-N,N-di(β-hydroxyethyl)aniline, 3-chloro-4-amino-N,N-di(β-hydroxyethyl)aniline, 4-amino-N-ethyl-N-(carbamoylmethyl)aniline, 3-methyl-4-amino-N-ethyl-N-(carbamoylmethyl)aniline, 4-amino-N-ethyl-N-(β-piperidinoethyl)aniline, 3-methyl-4-amino-N-ethyl-N-(β-piperidinoethyl)aniline, 4-amino-N-ethyl-N-(β-morpholinoethyl)aniline, 3-methyl-4-amino-N-ethyl-N-(β-morpholinoethyl)aniline, 4-amino-N-ethyl-N-(β-acetylaminoethyl)aniline, 4-amino-N-(β-methoxyethyl ) aniline, 3-methyl-4-amino-N-ethyl-N-(aminoethyl)aniline, 4-amino-N-ethyl-N-(β-mesylaminoethyl)aniline, 3-methyl-4-amino-N-ethyl-N-(β-mesylaminoethyl)aniline, 4-amino-N-ethyl-N-(β-sulphoethyl)aniline, 3-methyl-4-amino-N-ethyl-N-(β-sulphoethyl)aniline, N-(4'-aminophenyl)morpholine, N-(4'-aminophenyl)piperidine, 2-hydroxyethyl-para-phenylenediamine, fluoro-para-phenylenediamine, carboxy-para-phenylenediamine, sulpho-para-phenylenediamine, 2-isopropyl-para-phenylenediamine, 2-(n-propyl)-para-phenylenediamine, 2-hydroxymethyl-para-phenylenediamine, N,N-dimethyl- 3-methyl-para-phenylenediamine, N-ethyl-N-(β-hydroxy-ethyl)-para-phenylenediamine, N-dihydroxypropyl-para-phenylenedimine, N-(4'-aminophenyl)-para-phenylenediamine or N-phenyl-para-phenylenediamine.

These para-phenylenediamines can be introduced into the dyeing composition either in the form of the free base or in the form of salts, such as hydrochloride, hydrobromide or sulphate.

Among the para-aminophenols other than those of formula (I), there may be mentioned p-aminophenol, 2-methyl-4-aminophenol, 2-chloro-4-aminophenol, 3-chloro- 4-aminophenol, 2,6-dimethyl-4-aminophenol, 3,5-dimethyl-4-aminophenol, 2,3-dimethyl-4-aminophenol, 2,5-dimethyl 4-aminophenol, 2-(β-hydroxyethyl)-4-aminophenol, 2-methoxy-4-aminophenol, 3-methoxy-4-aminophenol, 3-(β-hydroxyethoxy)-4-aminophenol, 2-aminomethyl-4-aminophenol or 2-(β-hydroxyethylaminomethyl)-4-aminophenol.

The so-called "double" bases are bisphenylalkylenediamines corresponding to the formula:

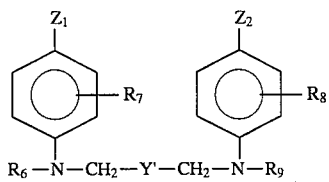

in which:

$Z_1$ and $Z_2$, which are identical or different, represent hydroxyl groups or groups $NHR_{10}$ where $R_{10}$ denotes a hydrogen atom or a lower alkyl radical;

$R_7$ and $R_8$, which are identical or different, represent either hydrogen atoms, or halogen atoms, or also alkyl radicals;

$R_6$ and $R_9$, which are identical or different, represent a hydrogen atom or an alkyl, hydroxyalkyl or aminoalkyl radical, it being possible for the amino residue to be substituted;

Y' represents a radical taken from the group consisting of the following radicals:

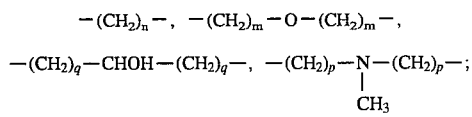

in which n is an integer between 0 and 8 and m, q and p are integers between 0 and 4, it also being possible for this base to be provided in the form of its addition salts with acids.

The alkyl or alkoxy radicals shown above preferably denote a group having 1 to 4 carbon atoms and especially methyl, ethyl, propyl, methoxy and ethoxy.

Among the compounds of formula (III), there may be mentioned N,N'-bis(β-hydroxyethyl)-N,N'-bis(4'-aminophenyl)- 1,3-diamino-2-propanol, N,N'-bis(β-hydroxyethyl)-N,N'-bis( 4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine.

The oxidation dye precursors of ortho type are chosen from ortho-aminophenols, such as 1-amino- 2-hydroxybenzene, 6-methyl-1-hydroxy-2-aminobenzene or 4-methyl-1-amino-2-hydroxybenzene, and ortho-phenylenediamines.

The compositions defined above, applied in the dyeing of keratinous fibres, can also contain, in addition to 6-hydroxyindole and/or 7-hydroxyindole used as couplers, other couplers known in themselves, such as meta-diphenols, meta-aminophenols, meta-phenylenediamines, meta-acylaminophenols, meta-ureidophenols, meta-carbalkoxyaminophenols, α-naphthol, or couplers having an active methylene group, such as β-ketone compounds or pyrazolones.

Among these couplers, there may be more particularly mentioned 2,4-dihydroxyphenoxyethanol, 2,4-dihydroxyanisole, meta-aminophenol, resorcinol monomethyl ether, resorcinol, 2-methylresorcinol, 2-methyl-5-aminophenol, N-(β-hydroxyethyl)-2-methyl-5-aminophenol, N-(β-mesylaminoethyl)-2-methyl-5-aminophenol, 2,6-di-methyl-3-aminophenol, 6-hydroxybenzomorpholine, 2,4-diaminoanisole, 2,4-diaminophenoxyethanol, 6-aminobenzomorpholine, [2-(β-hydroxyethyl)amino-4-amino]phenoxyethanol, 2-amino-4-[(β-hydroxyethyl)amino]anisole, 2,4-diaminophenyl β,γ-dihydroxypropyl ether, 2,4-diaminophenoxyethylamine, 1,3-dimethoxy-2,4-diaminobenzene, 1,3,5-trimethoxy-2,4-diaminobenzene, 1-amino-3,4-methylenedioxybenzene, 1-hydroxy-3,4-methylenedioxybenzene, 2-chloro-6-methyl-3-aminophenol, 2-methyl-3-aminophenol, 2-chlororesorcinol, 6-methoxy-3-hydroxyethylaminoaniline, 1-ethoxy-2-bis(β-hydroxyethyl)amino-4-aminobenzene, 3-diethylaminophenol, 1,3-dihydroxy-2-methylbenzene, 1-hydroxy-2,4-dichloro-3-aminobenzene, 4,6-hydroxyethoxy- 1,3-diaminobenzene, 4-methyl-6-ethoxy-1,3-diaminobenzene, 4-chloro-6-methyl-3-aminophenol, 6-chloro-3-trifluoroethylaminophenol and their salts.

There may be added to these compositions, as is well known in the state of the art, especially for the purpose of shading or enriching in highlights the colourings introduced by the para-aminophenol combined with 6-hydroxyindole and/or 7-hydroxyindole, direct dyes such as azo dyes, anthraquinone dyes or nitrated derivatives of the benzene series.

The combined oxidation dye precursors of para and/or ortho type, as well as the couplers used in the dyeing compositions used in the process according to the invention, preferably represent from 0.3 to 7% by weight with respect to the weight of the said composition.

The dyeing compositions used in the process according to the invention also contain, in their preferred embodiment, anionic, cationic, nonionic or amphoteric surface-active agents or their mixtures. Among these surface-active agents, there may be mentioned alkylbenzenesulphonates, alkyl-naphthalenesulphonates, sulphates, ether sulphates and fatty alcohol sulphonates, quaternary amonium salts such as trimethylcetylammonium bromide, or cetylpyridinium bromide, optionally oxyethylenated fatty acid ethanolamides, polyoxyethylenated acids, alcohols or amines, polyglycerolated fatty alcohols, polyoxyethylenated or polyglycerolated alkylphenols, and polyoxyethylenated alkyl sulphates.

These surface-active agents are present in the compositions in proportions of between 0.5 and 55% by weight, preferably between 2 and 50% by weight with respect to the total weight of the composition.

These compositions can also contain organic solvents for solubilising the components which would not be sufficiently soluble in water. Among these solvents, there may be mentioned, by way of example, $C_1$-$C_4$ lower alcohols, such as ethanol or isopropanol; glycerol; glycols or glycol ethers such as 2-butoxyethanol, ethylene glycol, propylene glycol and the monoethyl ether and the monomethyl ether of diethylene glycol, and the aromatic alcohols such as benzyl alcohol or phenoxy-ethanol, the analogous products and their mixtures.

The solvents are preferably present in proportions of between 1 and 40% by weight, and in particular between 5 and 30% by weight, with respect to the total weight of the composition.

The thickening agents which it is possible to add to the compositions used in the process according to the invention can be chosen from sodium alginate, gum arabic, optionally crosslinked acrylic acid polymers, cellulose derivatives or heterobiopolysaccharides such as xanthan gum. It is also possible to use inorganic thickening agents such as bentonite.

These thickening agents are preferably present in proportions of between 0.1 and 5%, and in particular between 0.2 and 3%, by weight with respect to the total weight of the composition.

The antioxidising agents which can be present in the compositions are chosen in particular from sodium sulphite, thioglycolic acid, sodium bisulphite, dehydroascorbic acid, hydroquinone and homogentisic acid.

These antioxidising agents are present in the composition in proportions of between 0.05 and 1.5% by weight with respect to the total weight of the composition.

These compositions can also contain other cosmetically acceptable adjuvants, such as, for example, penetration agents, sequestering agents, fragrances, buffers, dispersing agents, treatment agents, conditioning agents, film-forming agents, preserving agents, opacifying agents and the like.

The composition applied to the hair can be provided in various forms, such as in the liquid, cream or gel form or any other form suitable for carrying out dyeing of keratinous fibres and especially of human hair. These compositions can be packaged under pressure in aerosol containers in the presence of a propellant and to form-foams.

Another subject of the invention is the ready-to-use composition used in the process defined above.

According to a particularly preferred embodiment, the process comprises a preliminary stage consisting in storing in a separate form, on the one hand, the composition containing, in a medium suitable for dyeing, at least, as oxidation dye precursor, one para-aminophenol corresponding to the formula (I) defined above and, as coupler, 6-hydroxyindole and/or 7-hydroxyindole in the form of a component (A) and, on the other hand, a composition containing the oxidising agent as defined above in the form of a component (B), and in mixing them extemporaneously before applying this mixture to keratinous fibres, as shown above, the resulting composition having a pH value greater than 7 and preferably between 8 and 11.

In accordance with the invention, the dyeing process consists in applying the mixture obtained to hair, in leaving the mixture exposed for 10 to 40 minutes, preferably 15 to 30 minutes, and then rinsing the hair, washing it with the shampoo, rinsing it again and drying it.

It is also possible, in accordance with the invention, to apply separately a composition containing the para-aminophenol of formula (I), 6-hydroxyindole and/or 7-hydroxyindole and the oxidising agent which can be introduced, just before application, into the composition applied in the second stage or else be added to the keratinous fibres in a third stage, so that the mixture which forms in situ in the fibres has a pH greater than 7, the exposure, washing and drying conditions being the same as above.

Another subject of the invention is an agent for dyeing keratinous fibres, in particular human hair, essentially characterised in that it comprises at least two components, one of the components consisting of the composition (A) defined above and the other consisting of the composition (B), also defined above, the pH of the compositions (A) and (B) being such that, after mixing in proportions of 90 to 10% for the composition (A) and of 10 to 90% for the composition (B), the resulting composition has a pH greater than 7, and preferably of between 8 and 11.

The composition applied to keratinous fibres results in particular from a mixture of 10 to 90% of the component (A) with 90 to 10% of the component (B) containing an oxidising agent and has a pH greater than 7 and preferably of between 8 and 11.

This two-component dyeing agent can be packaged in a multi-compartment device or dyeing kit which constitutes another subject of the invention, or any other multi-compartment packaging system in which one of the compartments contains the component (A) and the second compartment contains the component (B); these devices can be equipped with a means making it possible to deliver the desired mixture to the hair, such as the devices described more particularly in patent U.S. Pat. No. 4,823,985 of the Applicant.

The examples which follow are intended to illustrate the invention without having in any way a limiting character.

EXAMPLES 1 TO 5

The dyeing of hair is carried out by applying, to permanent wave or non-permanent wave grey hair containing 90% white hairs, an extemporaneous mixture of the dyeing composition (A) and of the oxidising composition (B).

This mixture is left to act for 30 minutes, the hair is then rinsed and shampooing is carried out. After drying, the hair is dyed in the shade specified at the bottom of the table below.

| in g | 1 | 2 | 3 | 4 |
|---|---|---|---|---|
| A) Dyeing composition | | | | |
| 6-Hydroxyindole | 0.532 | 0.798 | 0.266 | |
| 7-Hydroxyindole | | | | 0.532 |
| 2-Methoxymethyl-4-aminophenol | 0.436 | 0.918 | 0.918 | 0.612 |
| 3-Amino-6-methylphenol | | | 0.246 | |
| 6-(α-hydroxyethoxy)-1,3-diaminobenzene | | | 0.482 | |
| Substrate 1 | | | X | X |
| Substrate 2 | X | X | | |
| Water qs | 100 | 100 | 100 | 100 |
| B) Oxidising composition | | | | |
| Hydrogen peroxide solution, 20 volumes | 100 | 100 | 100 | 100 |
| Phosphoric acid qs pH | 3 | 3 | 3 | 3 |
| 1/3 A + 2/3 B w/w mixture | | | X | |
| A + B w/w mixture | X | X | | X |
| pH of the mixture | 9.8 | 9.8 | 9.6 | 9.8 |
| Shades obtained on permanent wave hair containing 90% white hairs | coppery golden blonde | coppery dark blonde | coppery red chestnut dark blonde | strong iridescent blonde |

| in g | 5 | 6 | 7 | 8 |
|---|---|---|---|---|
| A) Dyeing composition | | | | |
| 6-Hydroxyindole | 0.532 | 0.532 | 0.532 | 0.266 |
| 2-Methoxymethyl-4-aminophenol | 0.612 | | | |
| 2-Ethoxymethyl-4-aminophenol hydrochloride | | 0.815 | | |
| 2-(β-hydroxyethoxymethyl)-4-aminophenol monohydrate monotartrate | | | 1.405 | |
| 2-Methylthiomethyl-4-aminophenol | | | | 0.338 |
| Substrate 3 | X | | | |
| Substrate 2 | | X | X | X |
| Water qs | 100 | 100 | 100 | 100 |
| B) Oxidising composition | | | | |
| Hydrogen peroxide solution, 20 volumes | 100 | 100 | 100 | 100 |
| Phosphoric acid qs pH | 3 | 3 | 3 | 3 |
| A + B w/w mixture | X | X | X | X |
| pH of the mixture | 10.0 | 9.5 | 9.5 | 9.8 |
| Shades obtained on non-permanent wave grey natural hair containing 90% white hairs | | | golden coppery | |
| On permanent wave grey natural hair containing 90% white hairs | strong golden coppery | strong coppery | | slightly golden cop- |

-continued

| | pery |
|---|---|
| COLOURING SUBSTRATE No. 1 | |
| Octyldodecanol sold under the name Eutanol G by the company Henkel | 8 g |
| Triethanolamine lauryl sulphate containing 40% of AM | 1.2 g AM |
| Ethyl alcohol | 10.5 g |
| Benzyl alcohol | 10 g |
| Oleocetyl alcohol oxyethylenated with 30 mol of ethylene oxide | 2.7 g |
| Cationic polymer in solution containing 60% of AM, consisting of recurrent units: | 2.22 g AM |

$$\left[\begin{array}{cc} CH_3 & CH_3 \\ | & | \\ -N^+-(CH_2)_3-N^+-(CH_2)_6- \\ | & | \\ CH_3 & CH_3 \\ Cl^- & Cl^- \end{array}\right]$$

| | |
|---|---|
| Monoethanolamine | 7.2 g |
| Linoleic acid diethanolamide sold under the name of Comperlan F by the company Henkel | 8 g |
| 20% Aqueous ammonia | 10.2 g |
| Aqueous sodium metabisulphite solution containing 35% of AM | 0.46 g AM |
| Hydroquinone | 0.15 g |
| 1-Phenyl-3-methyl-5-pyrazolone | 0.2 g |
| Sequestering agent qs | |
| COLOURING SUBSTRATE No. 2 | |
| Octyldodecanol sold under the name Eutanol G by the company Henkel | 8 g |
| Oleic acid | 20 g |
| Monoethanolamine lauryl ether sulphate sold under the name Sipon LM 35 by the company Henkel | 3 g |
| Ethyl alcohol | 10 g |
| Benzyl alcohol | 10 g |
| Cetearyl alcohol oxyethylenated with 33 mol of ethylene oxide, sold under the name Simulsol GS by the company Seppic | 2.4 g |
| Ethylenediaminetetraacetic acid | 0.2 g |
| Cationic polymer consisting of recurrent units, containing 60% of AM | 2.2 g AM |

$$\left[\begin{array}{cc} CH_3 & CH_3 \\ | & | \\ -N^+-(CH_2)_3-N^+-(CH_2)_6- \\ | & | \\ CH_3 & CH_3 \\ Cl^- & Cl^- \end{array}\right]$$

| | |
|---|---|
| Monoethanolamine | 7.5 g |
| Linoleic acid diethanolamide sold under the name Comperlan F by the company Henkel | 8 g |
| 20% Aqueous ammonia | 10.2 g |
| Aqueous sodium metabisulphite solution containing 35% of AM | 0.46 g AM |
| Hydroquinone | 0.15 g |
| 1-Phenyl-3-methyl-5-pyrazolone | 0.2 g |
| COLOURING SUBSTRATE No. 3 | |
| Oleic alcohol polyglycerolated with 2 mol of glycerol | 4 g |
| Oleic alcohol polyglycerolated with 4 mol of glycerol, containing 78% of AM | 5.7 g AM |
| Oleic acid | 3.0 g |
| Oleic amine oxyethylenated with 2 mol of ethylene oxide, sold under the name Ethomeen O 12 by the company Akzo | 7 g |
| Diethylaminopropyl laurylaminosuccinamate, sodium salt, containing 55% of AM | 3 g AM |
| Oleic alcohol | 5 g |
| Coconut oil acid diethanolamide | 12 g |
| Propylene glycol | 3.5 g |
| Dipropylene glycol | 0.5 g |
| Ethyl alcohol | 7.0 g |
| Propylene glycol monomethyl ether | 9 g |
| Aqueous sodium metabisulphite solution containing 35% of AM | 0.46 g AM |
| Ammonium acetate | 0.8 g |
| Monoethanolamine qs pH = 9.8 | |
| Antioxidising agent, sequestering agent qs | |

We claim:

1. Process for dyeing keratinous fibres, comprising applying to said fibres a mixture of at least one oxidation dye precursor comprising a para-aminophenol substituted in position 2 of the formula:

$$\underset{NH_2}{\underset{|}{\overset{OH}{\underset{|}{C_6H_3}}}}-CH_2YR \quad (I)$$

in which:

Y represents an oxygen atom or sulphur atom,

R represents a $C_1$-$C_4$ alkyl, $C_1$-$C_4$ monohydroxyalkyl or $C_2$-$C_4$ polyhydroxyalkyl radical, or their addition salts with an acid; and at least one coupler selected from the group consisting of 6-hydroxyindole, 7-hydroxyindole and mixtures thereof; a colour being developed at an alkaline pH in the presence of an oxidising agent.

2. Process according to claim 1, wherein said oxidising agent is hydrogen peroxide, urea hydrogen peroxide, alkali metal bromates or persalts.

3. Process according to claim 1, wherein R denotes a methyl, ethyl, propyl, iso-propyl, butyl or isobutyl radical or a mono- or a polyhydroxyalkyl radical of the formula $$CH_2-CH_2-OH, -CH_2-CHOH-CH_2-OH \text{ or } -CH_2-CHOH-CH_3.$$

4. Process according to claim 1, wherein the compound of formula (I) is 2-methoxymethyl-4-aminophenol, 2-ethoxymethyl-4-aminophenol, 2-propoxymethyl-4-aminophenol, 2-isopropoxymethyl-4-aminophenol, 2-(β-hydroxyethoxymethyl)-4-aminophenol, 2-methylthiomethyl-4-aminophenol, 2-(β-hydroxyethylthiomethyl)-4-aminophenol, 2-(β, γ-dihydroxypropylthiomethyl)-4-aminophenol, or their salts.

5. Process according to claim 1, wherein the coupler is 6-hydroxyindole.

6. Process according to claim 1, wherein the composition containing at least one para-aminophenol of formula (I) is applied in a first stage, the composition containing 6-hydroxyindole or 7-hydroxyindole or mixtures thereof is applied in a second stage, and the color is developed by applying the oxidising agent in the second stage or in a third stage, the pH of the mixture formed on fibres being greater than 7.

7. Oxidation dyeing process according to claim 1, wherein after application to keratinous fibres the resulting mixture is left on the fibres for 10 to 40 minutes, the fibres are rinsed, washed with a shampoo, rinsed again and dried.

8. Process according to claim 7, wherein the resulting mixture is left on the keratinous fibres for 15 to 30 minutes.

9. Process according to claim 1, wherein the keratinous fibres are human keratinous fibres.

10. Process according to claim 9, wherein the human keratinous fibres are human hair.

11. Process according to claim 1, wherein there is applied to keratinous fibres at least one composition (A) containing, in a medium suitable for dyeing, at least of one oxidation dye precursor comprising the para-aminophenol substituted in position 2 of formula (I) and at least one coupler selected from the group consisting of 6-hydroxyindole, 7-hydroxyindole and mixture thereof; the colour being developed at an alkaline pH in the presence of an oxidising agent present in the composition (A) or in a composition (B) containing said agent in a medium suitable for dyeing, said composition (B) being applied separately from the composition (A), either simultaneously or sequentially.

12. Process according to claim 11, wherein the pH of composition (A) or compositions (A) and (B) applied to keratinous fibres is such that the final pH of the fibres is between 8 and 11.

13. Process according to claim 11, wherein the composition (A) contains 0.05 to 3.5% by weight of the total weight of the composition of at least one compound of formula (I).

14. Process according to claim 11, wherein the composition (A) contains from 0.01 to 4% by weight, with respect to the total weight of the composition, of 6-hydroxyindole or 7-hydroxyindole or mixtures thereof.

15. Process according to claim 11, wherein the composition (A) contains, in addition to the at least one para-aminophenol of formula (I) other oxidation dye precursors selected from para-phenylenediamines, para-aminophenols other than those of formula (I), para heterocyclic precursors derived from pyridine or pyrimidine, ortho-aminophenols, ortho-phenylenediamines or bisphenylalkylenediamines.

16. Process according to claim 11, wherein the composition (A) contains, in addition to 6-hydroxtindole or 7-hydroxyindole or mixtures thereof, other couplers selected from meta-aminophenols, meta-phenylenediamines, meta-acylaminophenols, meta-ureidophenols, meta-carbalkoxyaminophenols, a-naphthol or couplers having an active methylene group.

17. Process according to claim 11, wherein the composition (A) contains from 0.3 to 7% by weight, with respect to the total weight of the composition, of the oxidation dye precursor and of the coupler.

18. Process according to claim 11, wherein the composition (A) contains cationic, anionic, nonionic or amphoteric surface-active agents or mixtures thereof, in concentrations of between 0.5 and 55% by weight with respect to the total weight of the composition; organic solvents in concentrations of between 1 and 40% by weight with respect to the total weight of the composition; thickening agents in concentrations of between 0.1 and 5% by weight with respect to the total weight of the composition; antioxidising agents in proportions of between 0.05 and 1.5% by weight with respect to the total weight of the composition, direct dyes, fragrances, sequestering agents, film-forming agents, treatment agents, dispersing agents, conditioning agents, preserving agents, or opacifying agents.

19. Process according to claim 11, wherein the compositions (A) and (B) are provided in liquid, cream or gel form or are packaged under pressure in aerosol containers in the presence of a propellant to form foams.

20. Agent for dyeing keratinous fibres comprising at least two components, one of the components consisting of the composition (A) defined in claim 11 and the other consisting of the composition (B) also defined in claim 11 the pH of the compositions (A) and (B) being such that, after mixing in proportions of 90 to 10% for the composition (A) and of 10 to 90% for the composition (B), the resulting composition has a pH greater than 7.

21. Composition for colouring keratinous fibres at basic pH, comprising the mixture of 10 to 90% of the composition (A) defined in claim 11 with 90 to 10% of the composition (B) defined in claim 11 having a pH greater than 7.

\* \* \* \* \*